(12) United States Patent
Langeland et al.

(10) Patent No.: US 8,326,007 B2
(45) Date of Patent: Dec. 4, 2012

(54) METHODS AND APPARATUS FOR COMBINED 4D PRESENTATION OF QUANTITATIVE REGIONAL MEASUREMENTS AND MORPHOLOGY

(75) Inventors: Stian Langeland, Vestfold (NO); Svein Brekke, Strusshamn (NO); Stein Rabben, Sofiemyr (NO); Andreas Heimdal, Oslo (NO)

(73) Assignee: General Electric Company, Schenectady, NY (US)

( * ) Notice: Subject to any disclaimer, the term of this patent is extended or adjusted under 35 U.S.C. 154(b) by 1123 days.

(21) Appl. No.: 12/119,372

(22) Filed: May 12, 2008

(65) Prior Publication Data
US 2009/0279763 A1 Nov. 12, 2009

(51) Int. Cl.
*G06K 9/00* (2006.01)
(52) U.S. Cl. ........ 382/128; 382/100; 382/131; 382/162; 382/154; 345/419
(58) Field of Classification Search .................. 382/128, 382/131, 100, 154, 162; 345/419
See application file for complete search history.

(56) References Cited

U.S. PATENT DOCUMENTS

| | | | | |
|---|---|---|---|---|
| 6,052,100 A * | 4/2000 | Soltan et al. | ...................... | 345/6 |
| 6,450,962 B1 * | 9/2002 | Brandl et al. | .................. | 600/458 |
| 6,757,423 B1 * | 6/2004 | Amini | ........................... | 382/154 |
| 7,035,480 B2 | 4/2006 | Akiyoshi et al. | | |
| 7,151,857 B2 | 12/2006 | Akiyoshi et al. | | |
| 2003/0197704 A1 | 10/2003 | Tek et al. | | |
| 2005/0096523 A1 | 5/2005 | Vass et al. | | |
| 2005/0152588 A1 | 7/2005 | Yoshida et al. | | |
| 2007/0129627 A1 * | 6/2007 | Profio et al. | .................. | 600/407 |
| 2008/0074427 A1 | 3/2008 | Barth | | |
| 2008/0077013 A1 | 3/2008 | Kawagishi et al. | | |
| 2008/0081998 A1 * | 4/2008 | Pan et al. | ...................... | 600/458 |

FOREIGN PATENT DOCUMENTS
WO WO 2006/088429 A1 8/2006

OTHER PUBLICATIONS

GE Healthcare Patent Application Specification, Methods and Apparatus for Volume Rendering, U.S. Appl. No. 11/800,742, filed May 7, 2007, (21) pages.
GE Healthcare Patent Application, Method for Motion Encoding of Tissue Structures in Ultrasonic Imaging, Patent No. 5,568,811, issued Oct. 29, 1996.

* cited by examiner

*Primary Examiner* — Andrew W Johns
*Assistant Examiner* — Shefali Goradia
(74) *Attorney, Agent, or Firm* — The Small Patent Law Group; Dean D. Small

(57) ABSTRACT

A method for combined 4D presentation of quantitative measurements and morphology of an object uses an apparatus that includes a computer or processor, memory, and a display. The method includes identifying a region of interest in volumetric image data. Then, the following steps are iterated to produce a 4D volume rendering. The iterated steps include tracking a wall of the object in the region of interest of the image data to produce a displacement field, applying the displacement field to display data to create enhanced rendering data, volume rendering the enhanced rendering data to produce an enhanced volume rendering, and displaying the enhanced volume rendering.

20 Claims, 11 Drawing Sheets
(3 of 11 Drawing Sheet(s) Filed in Color)

METHODS AND APPARATUS FOR COMBINED 4D PRESENTATION OF QUANTITATIVE REGIONAL MEASUREMENTS AND MORPHOLOGY

BACKGROUND OF THE INVENTION

This invention relates generally to methods and apparatus for presentation of quantitative measurements and morphology. The methods and apparatus are particularly useful in medical imaging.

New medical imaging technology permits regional quantitative 4D analysis of objects such as the myocardium of a patient's heart. The regional quantitative 4D analysis provides detailed information on the motion and deformation of all material points in the object. However, with this new imaging technology, there is a need for new display methods and apparatus. For example, there is a need for an intuitive display where a quantitative parameter is mapped directly to 3D anatomy. At least one known method for mapping parameters directly to 3D anatomy includes slicing of data and projecting the parameters onto a 2D image or projecting parametric data onto a surface model. This method simplifies the display of quantitative data, but does so at a cost of losing available detailed morphology information and visual perception of motion and deformation.

BRIEF DESCRIPTION OF THE INVENTION

In one aspect, some embodiments of the present invention provide a method for combined 4D presentation of quantitative measurements and morphology of an object. The method uses an apparatus that includes a computer or processor, memory, and a display. The method itself includes identifying a region of interest in volumetric image data. Then, the following steps are iterated to produce a 4D volume rendering. The iterated steps include tracking a wall of the object in the region of interest to produce a displacement field, applying the displacement field to display data to create enhanced rendering data, volume rendering the enhanced rendering data to produce an enhanced volume rendering, and displaying the enhanced volume rendering.

In another aspect, some embodiments of the present invention provide an apparatus that includes a computer or processor, memory, and a display. The apparatus is configured to identify a region of interest in volumetric image data. The apparatus further includes a tracking module configured to track a wall of the object in the image data of the region of interest of the object to produce a displacement field, a data lookup/registration module configured to apply the displacement field to display data to create enhanced rendering data, a volume rendering module configured to render the enhanced rendering data to produce an enhanced volume rendering, and a display configured to display the enhanced volume rendering. The tracking module, the data lookup/registration module and volume rendering module are configured to operate iteratively to thereby produce a 4D enhanced volume rendering.

In yet another aspect, some embodiments of the present invention provide a machine readable medium or media having recorded thereon instructions configured to instruct an apparatus that includes a computer or processor, memory, and a display. The instructions instruct the apparatus to identify a region of interest of the object, and repeat the following steps a plurality of times to produce a 4D enhanced volume rendering utilizing the volumetric image data. The repeated steps include tracking a wall of the object in the image data of the region of interest of the object to produce a displacement field, applying the displacement field to display data to create enhanced rendering data, volume render the enhanced rendering data to produce an enhanced volume rendering, and display the enhanced volume rendering.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION OF THE INVENTION

Figure 1:
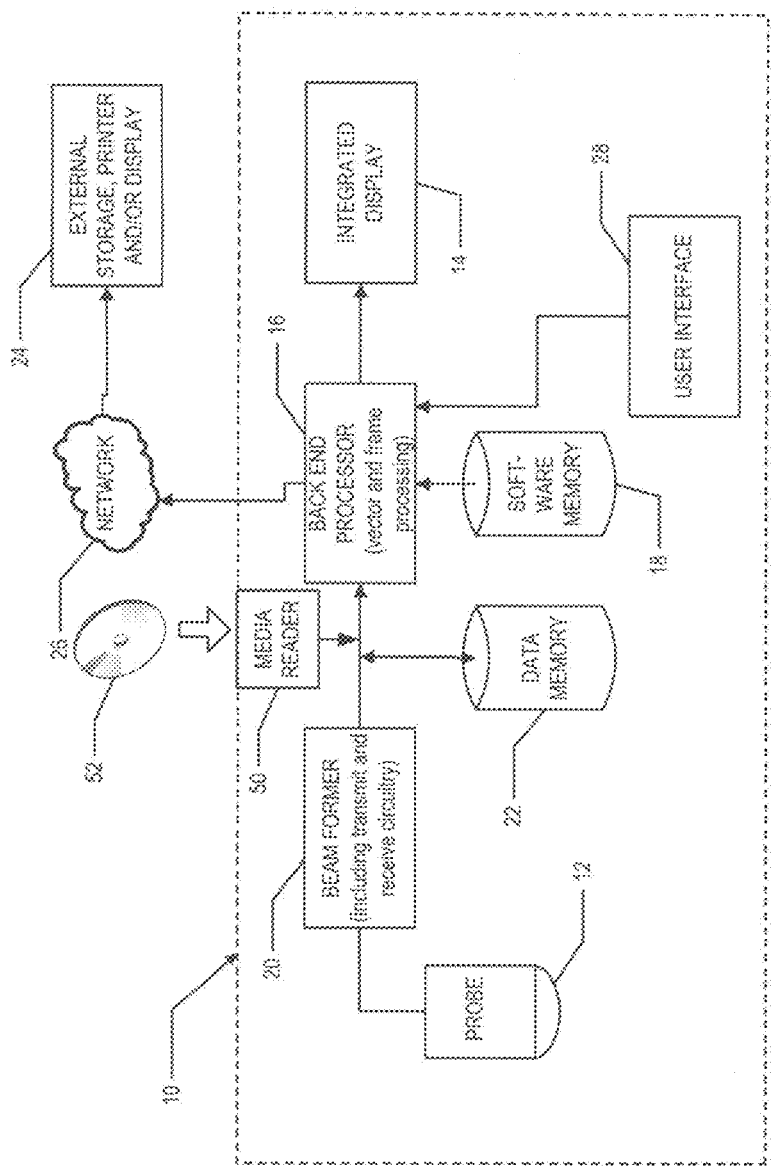
FIG. 1 is a block diagram of an ultrasound imaging apparatus formed in accordance with various embodiments of the invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property. Moreover, the terms "computer" and "processor" are used interchangeably herein to refer to either specialized hardware to perform digital signal processing, control, data manipulation, and/or calculations, or a general purpose computer that can be programmed to perform the same functions and/or adapted to interface with external digital signals. The phrases "computer or processor" and "processor or computer" are therefore intended to have equal scope with either of the individual terms and are not intended to imply a dichotomy between the two terms.

Technical effects of embodiments of the present invention include providing an improved quantitative data display while preserving detailed morphology. Furthermore, some embodiments of the present invention facilitate the use of any segmentation performed during extraction of quantitative parameters in improving a volume rendering display by removing information not related to an area of interest. This removal of information, when used in combination with color-coding of quantitative parameters, provides a highly intuitive display of quantitative data in 4D.

FIG. 1 is a block diagram of medical imaging system 10 having a probe or transducer 12 configured to acquire raw medical image data. In some embodiments, probe 12 is an ultrasound transducer and medical imaging system 10 is an ultrasound imaging apparatus. A display 14 (e.g., an internal display) is also provided and is configured to display a medical image. A data memory 22 stores acquired raw image data, which may be processed by a beam former 20 in some embodiments of the present invention.

To display a medical image using probe 12, a back end processor 16 is provided with a software or firmware memory 18 containing instructions to perform frame processing and scan conversion using acquired raw medical image data from probe 12, possibly further processed by beam former 20. Although shown separately in FIG. 1, it is not required that software memory 18 and data memory 22 be physically separate memories. Dedicated hardware may be used instead of software and/or firmware for performing scan conversion, or a combination of dedicated hardware and software, or software in combination with a general purpose processor or a digital signal processor. Once the requirements for such software and/or hardware and/or dedicated hardware are gained from an understanding of the descriptions of embodiments of the invention contained herein, the choice of any particular implementation may be left to a hardware engineer and/or software engineer. However, any dedicated and/or special purpose hardware or special purpose processor is considered subsumed in the block labeled "back end processor 16."

Software or firmware memory 18 can comprise a read only memory (ROM), random access memory (RAM), a miniature hard drive, a flash memory card, or any kind of device (or devices) configured to read instructions from a machine-readable medium or media 52. In some embodiments of the present invention, an accessible media reader 50 is provided. The instructions contained in software or firmware memory 18 further include instructions to produce a medical image of suitable resolution for display on display 14 and/or to send acquired raw or scan converted image data stored in a data memory 22 to an external device 24, such as a computer, and other instructions to be described below. The image data may be sent from back end processor 16 to external device 24 via a wired or wireless network 26 (or direct connection, for example, via a serial or parallel cable or USB port) under control of processor 16 and user interface 28. In some embodiments, external device 24 may be a computer or a workstation having a display and memory. User interface 28 (which may also include display 14) also receives data from a user and supplies the data to back end processor 16. In some embodiments, display 14 may include an x-y input, such as a touch-sensitive surface and a stylus (not shown), to facilitate user input of data points and locations.

Figure 2:
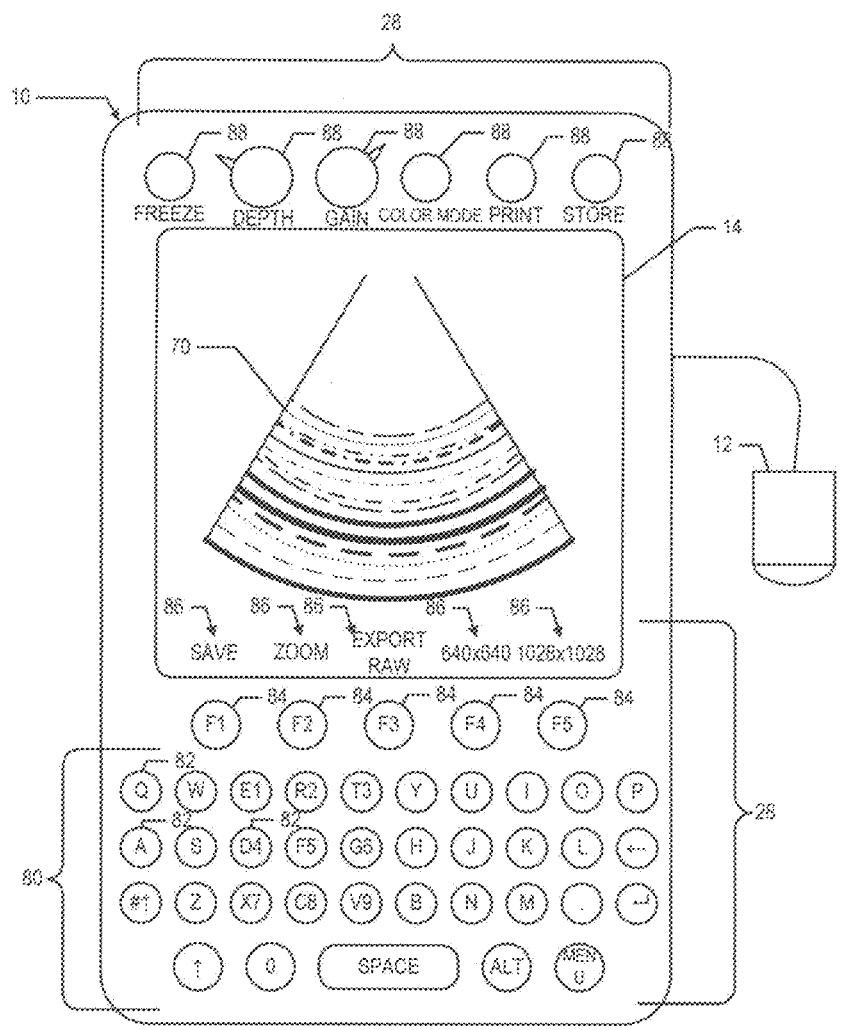
FIG. 2 is a pictorial view of a miniaturized ultrasound imaging apparatus formed in accordance with various embodiments of the invention.

FIG. 2 is a pictorial drawing of an embodiment of medical imaging system 10 configured as a hand-carried device. Hand carried medical imaging device 10 includes display 14, and the user interface 28. In some embodiments of the present invention, a typewriter-like keyboard 80 of buttons 82 is included in user interface 28, as well as one or more soft keys 84 that may be assigned functions in accordance with the mode of operation of medical imaging device 10. A portion of display 14 may be devoted to labels 86 for soft keys 84. For example, the labels shown in FIG. 2 allow a user to save the current raw medical image data, to zoom in on a section of image 70 on display 14, to export raw medical image data to an external device 24 (shown in FIG. 1), or to display (or export) an image. The device may also have additional keys and/or controls 88 for special purpose functions.

Figure 3:
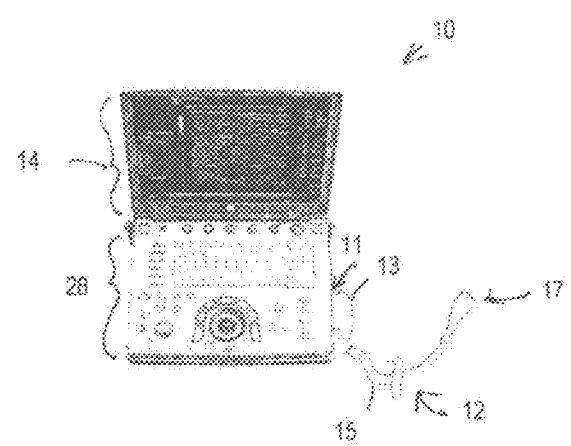
FIG. 3 is a pictorial view of a hand-held ultrasound imaging apparatus formed in accordance with various embodiments of the invention.

FIG. 3 illustrates an embodiment of medical imaging system 10 configured as a miniaturized device. As used herein, "miniaturized" means that the ultrasound system 10 is a hand-held or hand-carried device or is configured to be carried in a person's hand, briefcase-sized case, or backpack. For example, medical imaging system 10 may be a hand-carried device having a size of a typical laptop computer, for instance, having dimensions of approximately 2.5 inches in depth, approximately 14 inches in width, and approximately 12 inches in height. Medical imaging system 10 may weigh about ten pounds.

An ultrasound probe 12 has a connector end 13 that interfaces with ultrasound system 10 through an I/O port 11 on medical imaging system 10. Probe 12 has a cable 15 that connects connector end 13 and a scanning end 17 that is used to scan a patient. Medical imaging system 10 also includes a display 14 and user interface 28.

Embodiments of the present invention can comprise software or firmware instructing a computer to perform certain actions. Some embodiments of the present invention comprise stand-alone workstation computers that include memory, a display and a processor. The workstation may also include a user input interface (which may include, for example, a mouse, a touch screen and stylus, a keyboard with cursor keys, or combinations thereof). The memory may include, for example, random access memory (RAM), flash memory, or read-only memory. For purposes of simplicity, devices that can read and/or write media on which computer programs are recorded are also included within the scope of the term "memory." A non-exhaustive list of media that can be read with such a suitable device includes CDs, CD-RWs, DVDs of all types, magnetic media (including floppy disks, tape, and hard drives), flash memory in the form of sticks, cards, and other forms, ROMs, etc., and combinations thereof.

Some embodiments of the present invention may be incorporated into a medical imaging apparatus, such as ultrasound imaging system 10 of FIG. 1. In correspondence with a stand-alone workstation, the "computer" can be considered as the apparatus itself or at least a portion of the components therein. For example, back end processor 16 may comprise a general purpose processor with memory, or a separate processor and/or memory may be provided. Display 14 corresponds to the display of the workstation, while user interface 28 corresponds to the user interface of the workstation. Whether a stand-alone workstation or an imaging apparatus is used, software and/or firmware (hereinafter referred to generically as "software") can be used to instruct the computer to perform the inventive combination of actions described herein. Portions of the software may have specific functions and these portions are herein referred to as "modules" or "software modules." However, in some embodiments, these modules may comprise one or more electronic hardware components or special-purpose hardware components that may be configured to perform the same purpose as the software module or to aid in the performance of the software module. Thus, a "module" may also refer to hardware or a combination of hardware and software performing a function.

Figure 4:
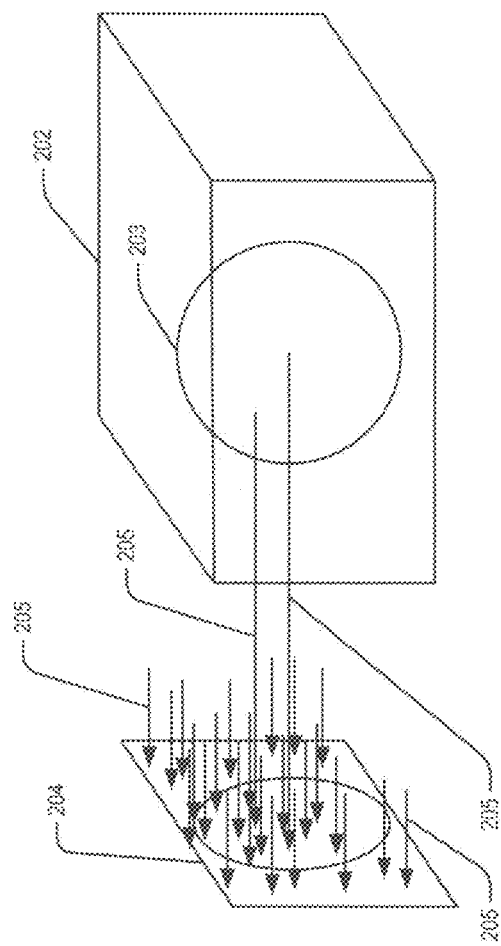
FIG. 4 is a drawing illustrating a method of visualization by volume rendering.

Visualization by volume rendering is a well-known technique for producing realistic images of volumetric objects 203. As shown in FIG. 4, volume rendering may be performed by casting rays 205 through a volume of interest 202. The "ray value" recorded in image plane 204 is a combination of the values of all or some of the voxels met along the path through the volume of interest 202 to the image plane 204, thus the name "volume rendering." In various embodiments of the present invention, the combination is the sum of the voxel values each multiplied by a weighting factor called the "opacity function" or, more generally, a "transfer function." Further, other volume rendering techniques, such as object order rendering (projection of planes or voxels in the dataset into the view plane) may be used instead of ray tracing. By taking advantage of material tracking, enhanced volume rendering with preserved visual perception of motion and deformation can be generated.

Figure 5:
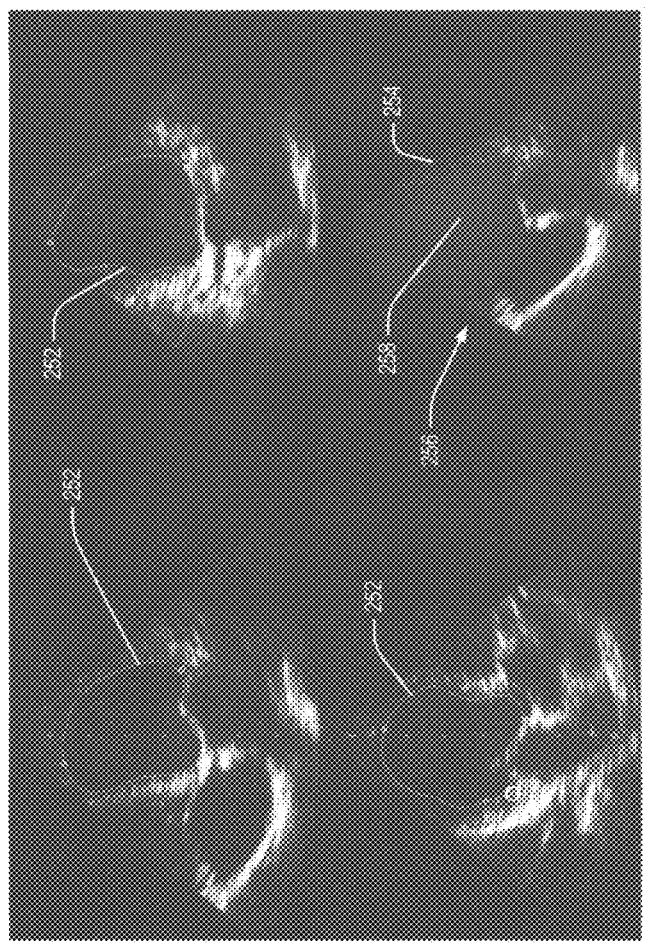
FIG. 5 is a drawing illustrating boundaries and a surface model output by a 3D segmentation algorithm that is configured to detect the boundary of a volumetric object in accordance with various embodiments of the invention.

FIG. 5 is a drawing illustrating boundaries 252 and a surface model 254 output by a 3D segmentation algorithm that is configured to detect the boundary of a volumetric object 256. In the examples used herein, the images are echocardiographic images (i.e., ultrasound images of a heart 256) and the volumetric object is the left ventricle 258. Some embodiments of the invention either provide or require as a prerequisite, a segmentation and tracking algorithm for volumetric image data.

Figure 6:
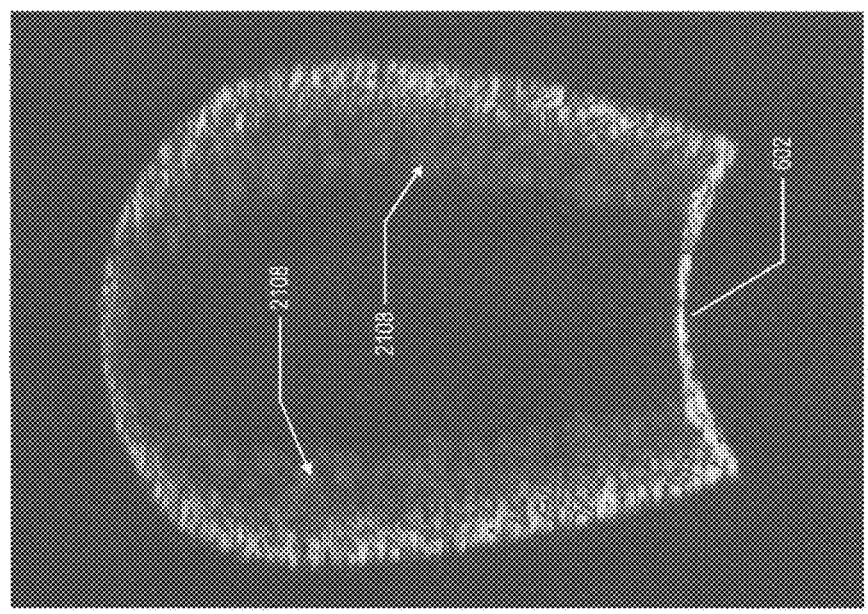
FIG. 6 is an illustration of a displacement field produced by the tracking shown in 2D.

FIG. 6 is a drawing illustrating a displacement field 2108. Displacement field 2108 can be estimated using a suitable tracking method. Displacement field 2108 is shown here on a 2D image 602 for simplicity.

Figure 7:
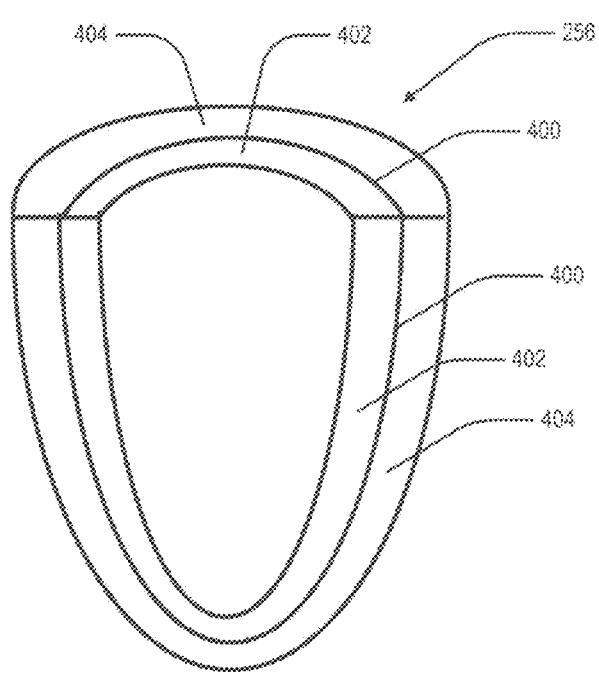
FIG. 7 is a schematic drawing of a object boundary of a cavity showing image data regions on either side of the boundary.

FIG. 7 is a schematic drawing of a segmented object 256 representing an object boundary 400 showing image data regions 402, 404 on either side of boundary 400. Some embodiments of the present invention use a morphologically accurate volume rendering to display quantitative measurements in combination with display data. Such a display is particularly useful in visualizing myocardial motion and deformation.

Figure 8:
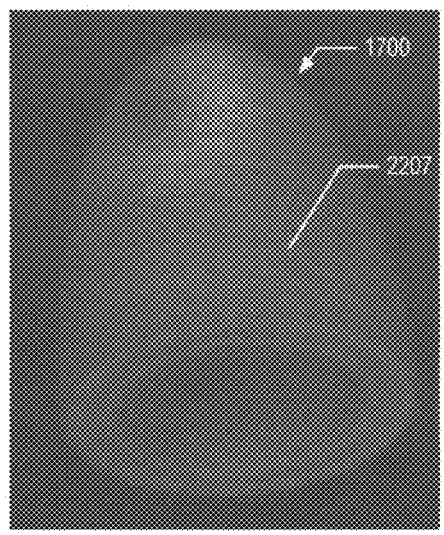
FIG. 8 is a volume rendering (based on a simulation) that has been optimized using segmentation.

In some embodiments used for visualizing myocardial motion and deformation, a volume rendering is generated from volumetric data that is optimized or at least improved using segmentation from 3D strain in which both endocard and a rough estimate of epicard is detected. A simulation 1700 illustrating an image resulting from volume rendering optimized using segmentation is shown in FIG. 8. A similar display results from embodiments in which volume rendering is generated from synthetically generated 4D data based on results of segmentation and material tracking.

Figure 9:
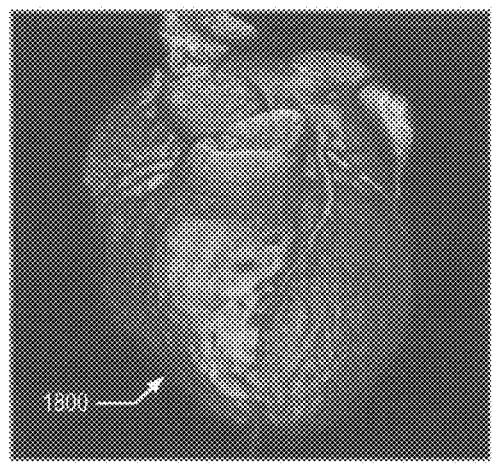
FIG. 9 is an example of a still frame 3D CT volume rendering that can be registered using a displacement field.

In some other embodiments used for visualizing myocardial motion and deformation, the volume rendering is generated from still frame 3D data obtained from other imaging modalities (e.g., MRI, 3D CT, etc.). An example of such a still frame 1800 obtained from 3D CT is shown in FIG. 9. Some other embodiments use volume rendering generated from an artificial cardiac model, with deformation based upon an estimated displacement field.

Figure 10:
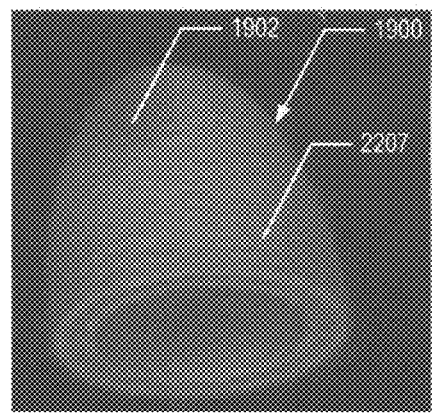
FIG. 10 is a volume rendering optimized using segmentation with superimposed longitudinal strain as seen from outside a wall of an object.
Figure 11:
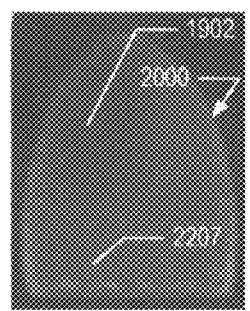
FIG. 11 is a volume rendering optimized using segmentation with superimposed longitudinal strain as seen from the inside of an object.

In some embodiments of the present invention, the object in the volume rendering is color-coded based on estimated quantitative parameters. FIG. 10 and FIG. 11 are illustrations of such a color coding. FIG. 10 illustrates a volume rendering 1900 optimized using the tracking with superimposed longitudinal strain 1902 as seen from outside the wall. FIG. 11 is the same segmentation with the same superimposed longitudinal strain 1902, but is a cropped view 2000 as seen from inside the wall.

Figure 12:
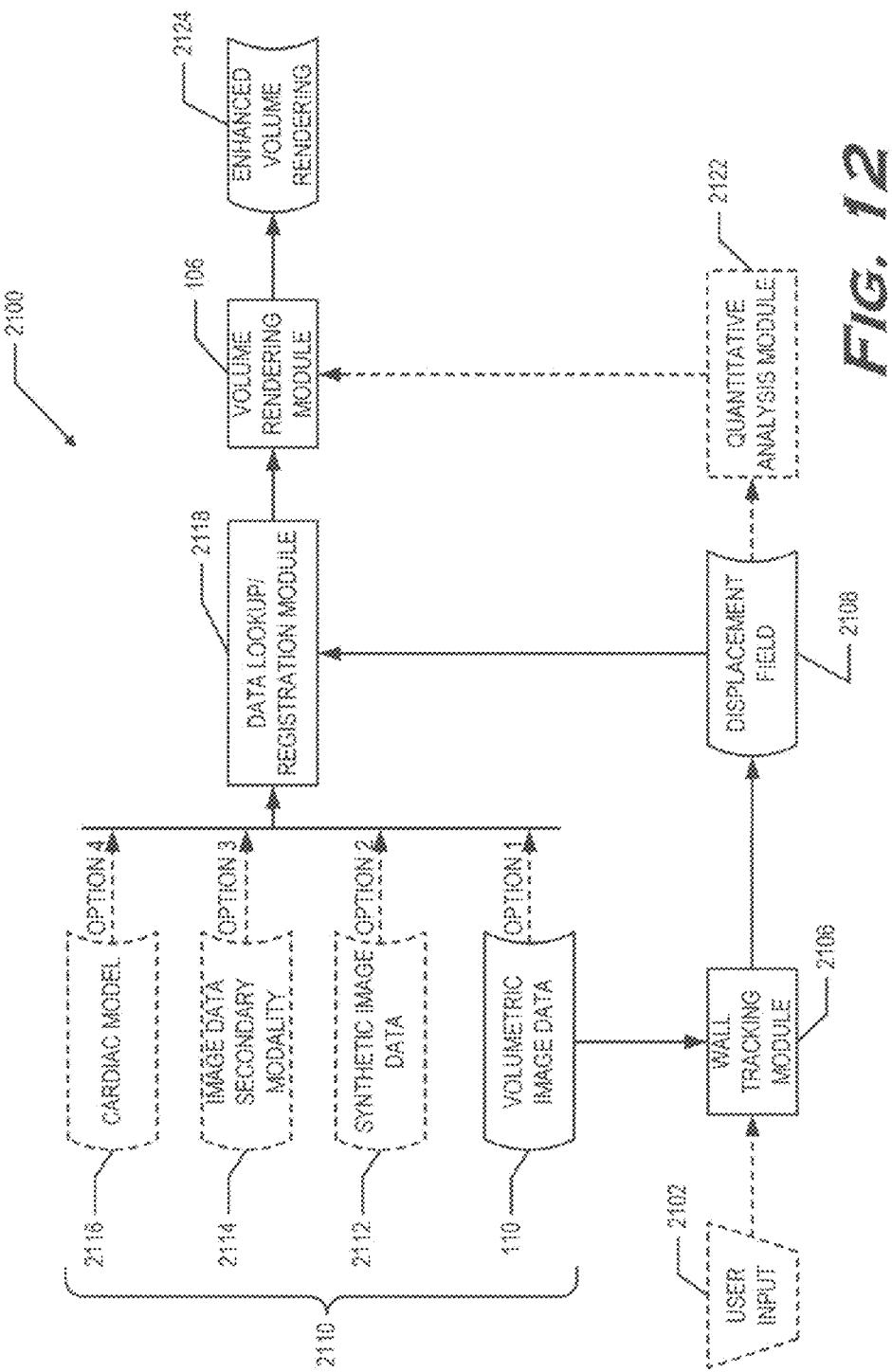
FIG. 12 is a block diagram illustrating the operation of one embodiment of the present invention.

FIG. 12 is a block diagram 2100 of one embodiment of the present invention. User input 2102 and image data 110 are provided to a wall tracking module 2106, which at least initially determines walls depicted within an area of interest of image data 110. User input 2102 is not necessarily required for all embodiments of the present invention, and some embodiments need not provide any functionality for gathering user input 2102, optionally or otherwise. User input 2102, when provided, includes initialization data, such as a manual or semi-automated segmentation of one or more walls. Wall tracking module 2106 can be any known method that can be used to track an object in image data 110 and produce a displacement field 2108 within the wall.

A data lookup/registration module 2118 is provided to process the display data 2110 and the displacement field 2108 produced by wall tracking module 2106. The term "display data," as used herein, may comprise any one or more of image data 110, synthetic image data 2112, a secondary (or tertiary, etc.) modality of image data 2114 (for example, a CT or MRI image), and a cardiac model 2116 or other volumetric anatomical model. Embodiments of the present invention thus may provide, but are not required to provide, more than one set of data to be displayed 2110. Embodiments that do provide more than one set of data to be displayed 2110 may provide, but are not required to provide, a choice of which set of data 2110 is to be displayed. Data lookup/registration module 2118 applies the displacement field 2108 to the display data 2110 to deform the display data accordingly. The result is fed into a volume rendering module 106 to produce an enhanced volume rendering 2124 of the display data 2110, showing displacements of walls within that data.

Some embodiments of the present invention also provide a quantitative analysis module 2122 that extracts at least one quantitative parameter from displacement field 2108. Thus, some embodiments apply one or more of these quantitative parameters extracted from displacement field 2108 to enable volume rendering module 106 to superimpose color coded data on volume rendering 2124.

Figure 13:
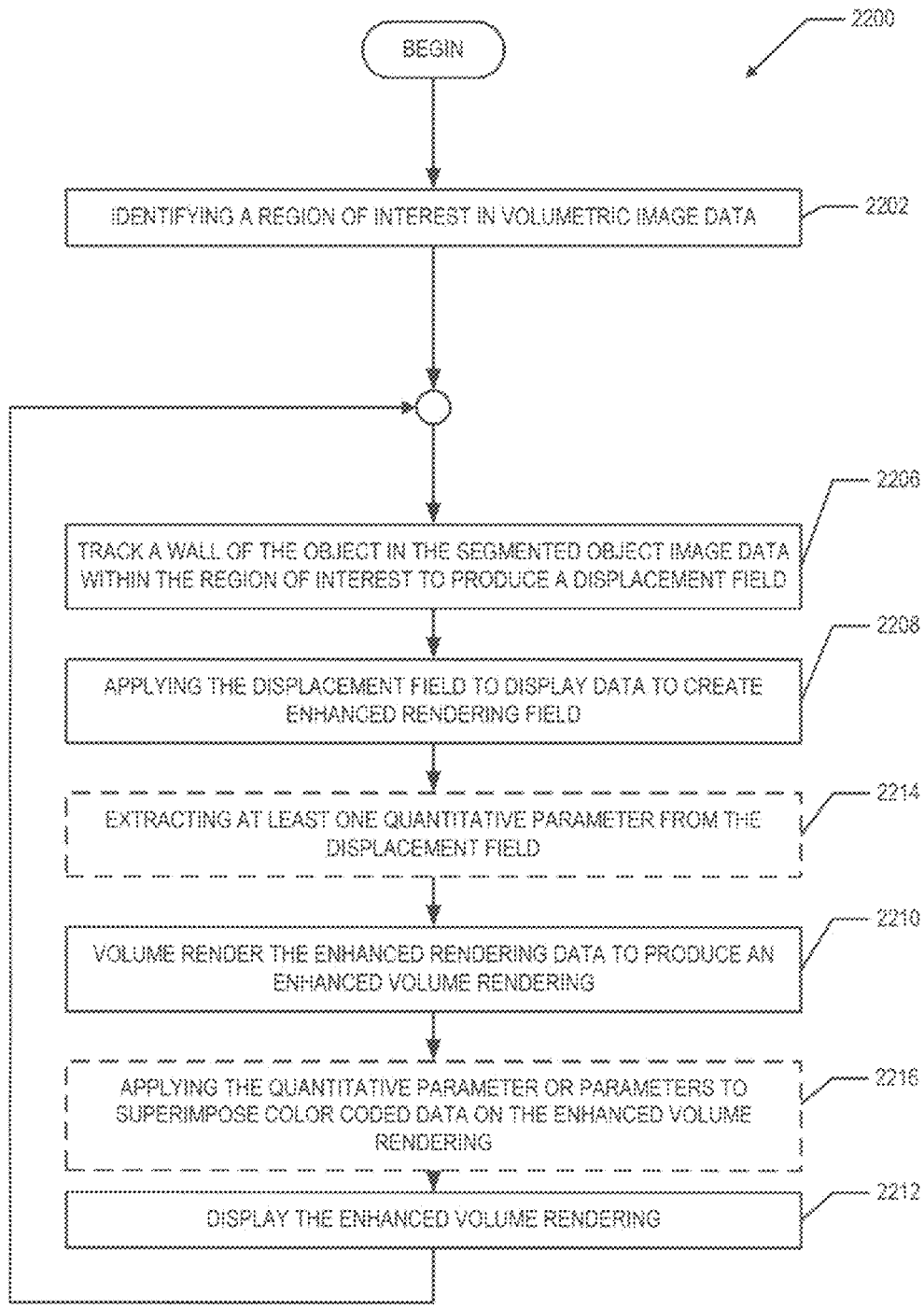
FIG. 13 is a flow chart of the operation of one embodiment of the present invention that results in display of volume rendered data.

More particularly, some embodiments of the present invention provide a method for improving the user's visual perception of object deformation by enhancing the 4D presentation of measurements and morphology of an object 256. The method uses an apparatus 10 comprising a computer or processor 16, memory 22, and a display 14. FIG. 13 is a flow chart 2200 that illustrates the method. The method includes, at 2202, identifying a region of interest of an object 256 in volumetric image data 110. The identifying may be performed by a processor 16 and a memory 22, and may also include display 14 and user interface 28. The identification may be as represented in FIG. 5, and may be performed by wall tracking module 2106. The identification of the region of interest of object 256 need only be done once, whereas the following steps are iterated with each incoming set of volumetric image data 110. Next, at 2206, a wall 2207 (see FIGS. 8, 10, and 11) of object 256 is tracked in volumetric image data 110 within the region of interest 202 of the object 256 to produce a displacement field 2108. Next, at 2208, displacement field 2108 is applied display data 2110 to create an enhanced volume rendering 2114. The enhanced volume rendering is then displayed on a display 14 at 2212. Processing continues at 2206 to thereby produce a 4D enhanced volume rendering utilizing the tracked volumetric image data.

Variations of the method recited above are used in some embodiments of the present invention. For example, in some embodiments, display data 2110 includes the image data 110 of the region of interest of the object 256. Furthermore, in some embodiments, display data 2110 includes data related to the morphology of the object, which itself may include at least one of still frame 3D data 2114 from an image modality other than ultrasound imaging, an artificial 3D model of a heart 2116, and/or synthetic image data of a heart 2112. Furthermore, in some embodiments, the volumetric image data is ultrasound image data.

In some variant embodiments of the method, object 256 is a patient's heart, and display data 2110 includes at least one of still frame 3D data 2114 from an image modality other than ultrasound imaging, an artificial 3D model of a heart 2116, and synthetic image data of a heart 2112. The modality other than ultrasound imaging may be, for example, magnetic resonance imaging and/or 3D computed tomographic imaging.

Some variant embodiments of the method further include, at 2214, extracting at least one quantitative parameter from the displacement field and, at 2216, applying the quantitative parameter or parameters to superimpose color coded data 1904 on the enhanced volume rendering 1900 or 2000.

It should be noted that configurations of the present invention are not limited to cardiac applications or medical applications, in which case the data 2110 to be displayed would be data representative of a different object having different displacement characteristics.

In some embodiments of the present invention, an apparatus 10 is provided that includes a computer or processor 16, memory 18 and 22, and a display 14. The apparatus 10 is configured (such as by program software and/or firmware as well as structurally) to identify a region of interest in volumetric image data 110 of an object. Apparatus 10 further includes modules that may be implemented within the processor or computer by a stored program and/or within special purpose hardware. These modules include tracking module 2106 configured to track a wall 2207 of the object 256 in image data 110 to produce a displacement field 2108. Also included is a data lookup/registration module 2118 configured to register the displacement field 2108 with the display image data 2110 that includes at least one of the image data 110 of the region of interest 202 of the object 256 and data 2112, 2114, 2116 related to morphology of the object 256 to create enhanced rendering data, and a volume rendering module 106 configured to render the enhanced rendering data to produce an enhanced volume rendering 2124. The apparatus further includes a display 14 configured to display the enhanced volume rendering 2124. The tracking module 2106, the data lookup/registration module 2118 and the volume rendering module 106 are configured to operate iteratively to thereby produce an enhanced volume rendering 2124 utilizing the volumetric image data.

In some embodiments, the stored data 2110 in the apparatus includes image data 110 of the region of interest 202 of the object 256. Also, in some other embodiments, the stored data 2110 includes data 2112, 2114, and/or 2116 related to the morphology of the object. Also, in some embodiments, the apparatus 10 is an ultrasound imaging apparatus that includes an ultrasound probe 12. Apparatus 10 is configured to obtain 4D image data using the ultrasound probe 12, and the 4D image data is ultrasound image data. In some of these embodiments, the stored data 2110 includes still frame 3D data 2114 from an image modality other than ultrasound imaging, an artificial 3D model 2116 of a heart, and/or synthetic image data 2112 of a heart. In some of these embodiments, the modality other than ultrasound imaging includes magnetic resonance imaging and/or 3D computed tomographic imaging.

Some variant embodiments of apparatus 10 further include a quantitative analysis module 2122 configured to extract at least one quantitative parameter from the displacement field 2108 and to apply the quantitative parameter or parameters to superimpose color coded data on the enhanced volume rendering 2124.

In yet other embodiments of the present invention, a machine readable medium or media 52 (such as, but not limited to, magnetic disks and diskettes, optical disks and diskettes, and/or ROM, flash ROM, and/or battery backed RAM, or any other suitable magnetic, optical, or electronic medium or media) is provided along with one or more suitable media readers 50. The medium (or media) 52 has recorded thereon instructions configured to instruct an apparatus 10 that includes a computer or processor 16, memory 18, 22, and a display 14. The instructions include instructions to identify a region of interest 256 in volumetric image data 110. The instructions further include instructions to repeat the following steps a plurality of times. The repeated steps include tracking a wall 2207 of the object 256 in the image data 110 of the region of interest 202 of the object 256 to produce a displacement field 2108, applying the displacement field 2108 to the display data 2110 to create enhanced rendering data, and volume rendering the enhanced rendering data to produce an enhanced volume rendering 2124. The repeated instructions further include displaying the enhanced volume rendering 2124. The repetition thus produces a 4D enhanced volume rendering utilizing the volumetric image data.

In a variant embodiment, the medium or media 52 further include instructions configured to instruct an ultrasound imaging apparatus 10 having an ultrasound probe 12. These instructions include instructions for the ultrasound imaging apparatus to obtain 4D image data using the ultrasound probe 12, where the 4D image data is ultrasound image data. In yet another variant embodiment, the medium or media 52 have instructions recorded thereon to instruct the apparatus to repeatedly extract at least one quantitative parameter from the displacement field and repeatedly apply the quantitative parameter or parameters to superimpose color coded data on the enhanced volume rendering 2124. The results of such color coding can be seen in FIG. 10 and FIG. 11.

In yet another variant embodiment, display data 2110 of the region of interest 202 of the object 256 and/or data 2112, 2114, and/or 2116 related to morphology of the object 256 specifically includes the image data 110 of the region of interest 202 of the object 256. In still another variant embodiment, display data 2110 of the region of interest 202 of the object 256 and/or data 2112, 2114, and/or 2116 related to morphology of the object 256 specifically includes data 2112, 2114, and/or 2116 related to the morphology of the object.

It will thus be appreciated that embodiments of the present invention provide an intuitive display of a parameter mapped onto the morphology of an object without losing available detailed morphology information. By removing information not related to the area of interest, volume rendering is improved and a more intuitive display can be provided. Embodiments of the present invention are particularly useful for producing morphologically accurate volume renderings that display myocardial motion and deformation.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for combined 4D presentation of quantitative measurements and morphology of an object, using an apparatus comprising a computer or processor, memory, and a display, said method comprising:
    identifying a region of interest in volumetric image data;
    repeating the following steps a plurality of times:
    tracking a wall of the object in the region of interest of the image data to produce a displacement field;
    applying the displacement field to display data to deform the display data and create enhanced rendering data showing displacement of the wall within the display data;
    volume rendering the enhanced rendering data to produce an enhanced volume rendering;
    extracting at least one quantitative parameter from the displacement field;
    applying said at least one quantitative parameter to superimpose color coded data on the enhanced volume rendering; and
    displaying the enhanced volume rendering;
    wherein said repetition produces a 4D enhanced volume rendering.

2. The method of claim 1 wherein said display data comprises the region of interest of the object.

3. The method of claim 1 wherein said display data comprises data related to the morphology of the object.

4. The method of claim 1 wherein the volumetric image data is ultrasound image data.

5. The method of claim 4 wherein the object is a patient's heart and display data comprises at least one of still frame 3D data from an image modality other than ultrasound imaging, an artificial 3D model of a heart, and synthetic image data of a heart.

6. The method of claim 5 wherein said modality other than ultrasound imaging comprises at least one of magnetic resonance imaging and 3D computed tomographic imaging.

7. The method of claim 1 wherein the object is a heart.

8. The method of claim 1 wherein said at least one quantitative parameter comprises longitudinal strain.

9. An apparatus comprising a computer or processor, memory, and a display, said apparatus configured to:
    identify a region of interest of an object in volumetric image data;
    said apparatus further including:
    a tracking module configured to track a wall of the object in the region of interest to produce a displacement field;
    a data lookup/registration module configured to apply the displacement field to display data to deform the display data and create enhanced rendering data showing displacement of the wall within the display data;
    a volume rendering module configured to render the enhanced rendering data to produce an enhanced volume rendering;
    a quantitative analysis module configured to extract at least one quantitative parameter from the displacement field and to apply said at least one quantitative parameter to superimpose color coded data on the enhanced volume rendering; and
    a display configured to display the enhanced volume rendering,
    wherein the tracking module, the data lookup/registration module and volume rendering module are configured to operate iteratively to thereby produce a 4D enhanced volume rendering.

10. The apparatus of claim 9 wherein said display data comprises the region of interest of the object.

11. The apparatus of claim 9 wherein said display data comprises data related to the morphology of the object.

12. The apparatus of claim 9 wherein the apparatus is an ultrasound imaging apparatus further comprising an ultrasound probe, said apparatus is configured to obtain 4D image data using the ultrasound probe, and the 4D image data is ultrasound image data.

13. The apparatus of claim 12 wherein said display data comprises at least one of still frame 3D data from an image modality other than ultrasound imaging, an artificial 3D model of a heart, and synthetic image data of a heart.

14. The apparatus of claim 13 wherein said modality other than ultrasound imaging comprises at least one of magnetic resonance imaging and 3D computed tomographic imaging.

15. The apparatus of claim 9 wherein said at least one quantitative parameter comprises longitudinal strain.

16. A non-transitory machine readable medium or media having recorded thereon instructions configured to instruct an apparatus comprising a computer or processor, memory, and a display, to:
    identify a region of interest of an object;

repeat the following steps a plurality of times:
track a wall of the object in the region of interest to produce a displacement field;
apply the displacement field to display data to deform the display data and create enhanced rendering data showing displacement of the wall within the display data;
volume render the enhanced rendering data to produce an enhanced volume rendering;
extract at least one quantitative parameter from the displacement field;
apply said at least one quantitative parameter to superimpose color coded data on the enhanced volume rendering; and
display the enhanced volume rendering;
wherein said repetition produces a 4D enhanced volume rendering utilizing the 4D image data.

17. The non-transitory machine readable medium or media of claim 16 wherein the instructions are configured to instruct an ultrasound imaging apparatus having an ultrasound probe, said instruction further including instructions for the ultrasound imaging apparatus to obtain 4D image data using the ultrasound probe, and wherein the 4D image data is ultrasound image data.

18. The non-transitory machine readable medium or media of claim 16 wherein said at least one quantitative parameter comprises longitudinal strain.

19. The non-transitory machine readable medium or media of claim 16 wherein said display data comprises the region of interest of the object.

20. The non-transitory machine readable medium or media of claim 16 wherein said display data comprises data related to the morphology of the object.

* * * * *